(12) United States Patent
Matsui et al.

(10) Patent No.: US 10,667,676 B2
(45) Date of Patent: Jun. 2, 2020

(54) ELECTRONIC ENDOSCOPE AND ENDOSCOPE SYSTEM THAT SETS A GAIN PARAMETER ACCORDING TO A GAMMA CHARACTERISTIC OF A CONNECTED PROCESSOR

(71) Applicant: OLYMPUS CORPORATION, Tokyo (JP)

(72) Inventors: Yasunori Matsui, Hino (JP); Shinji Yamashita, Tachikawa (JP); Yuzuru Tanabe, Niiza (JP); Yuta Matsuno, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 19 days.

(21) Appl. No.: 16/220,739

(22) Filed: Dec. 14, 2018

(65) Prior Publication Data
US 2019/0133426 A1 May 9, 2019

Related U.S. Application Data

(63) Continuation of application No. PCT/JP2017/008328, filed on Mar. 2, 2017.

(30) Foreign Application Priority Data

Sep. 1, 2016 (JP) .................. 2016-170784

(51) Int. Cl.
*H04N 5/20* (2006.01)
*A61B 1/05* (2006.01)
(Continued)

(52) U.S. Cl.
CPC ............ *A61B 1/05* (2013.01); *A61B 1/00009* (2013.01); *A61B 1/00188* (2013.01);
(Continued)

(58) Field of Classification Search
CPC .................. G06T 2207/10068; A61B 1/00006
See application file for complete search history.

(56) References Cited

U.S. PATENT DOCUMENTS

2001/0007468 A1* 7/2001 Sugimoto .......... A61B 1/00045
348/71
2002/0177751 A1* 11/2002 Ueno ................. A61B 1/00009
600/160
(Continued)

FOREIGN PATENT DOCUMENTS

EP 2053862 A1 4/2009
EP 2987449 A1 2/2016
(Continued)

OTHER PUBLICATIONS

International Search Report dated May 30, 2017 issued in PCT/JP2017/008328.

*Primary Examiner* — Gary C Vieaux
(74) *Attorney, Agent, or Firm* — Scully, Scott, Murphy & Presser, P.C.

(57) ABSTRACT

An electronic endoscope removably connected to a video processor in which a predetermined gamma characteristic is set includes: an image pickup device provided at a distal end of an insertion portion configured to be inserted into a subject, the image pickup device being configured to pick up an optical image of the subject to generate an image pickup signal; a gain circuit configured to amplify the image pickup signal using a predetermined gain parameter; a gamma characteristic recognition circuit configured to recognize the gamma characteristic of the video processor; and a gain adjustment circuit configured to set the gain parameter according to the gamma characteristic.

8 Claims, 4 Drawing Sheets

(51) Int. Cl.
    *A61B 1/045*     (2006.01)
    *H04N 7/18*     (2006.01)
    *A61B 1/00*     (2006.01)
    *A61B 90/30*     (2016.01)
    *A61B 1/06*     (2006.01)
    *H04N 5/225*     (2006.01)

(52) U.S. Cl.
    CPC .............. *A61B 1/045* (2013.01); *A61B 90/30* (2016.02); *H04N 7/18* (2013.01); *H04N 7/185* (2013.01); *A61B 1/0684* (2013.01); *A61B 2090/308* (2016.02); *G06T 2207/10016* (2013.01); *G06T 2207/10068* (2013.01); *H04N 2005/2255* (2013.01); *H04N 2201/0079* (2013.01)

(56) References Cited

U.S. PATENT DOCUMENTS

| | | |
|---|---|---|
| 2003/0222997 A1 | 12/2003 | Iketani |
| 2009/0105544 A1 | 4/2009 | Takahira |
| 2014/0036051 A1 | 2/2014 | Saito et al. |
| 2016/0029874 A1 | 2/2016 | Usami |

FOREIGN PATENT DOCUMENTS

| | | |
|---|---|---|
| JP | 2003339636 A | 12/2003 |
| JP | 2004181231 A | 7/2004 |
| JP | 2007117153 A | 5/2007 |
| JP | 2009100935 A | 5/2009 |
| JP | 2011152300 A | 8/2011 |
| JP | 2016158940 A | 9/2016 |
| JP | 2016209113 A | 12/2016 |
| JP | 6058235 B1 | 1/2017 |
| WO | 2013128764 A1 | 9/2013 |
| WO | 2014171332 A1 | 10/2014 |
| WO | 2016185734 A1 | 11/2016 |

* cited by examiner

ELECTRONIC ENDOSCOPE AND ENDOSCOPE SYSTEM THAT SETS A GAIN PARAMETER ACCORDING TO A GAMMA CHARACTERISTIC OF A CONNECTED PROCESSOR

CROSS REFERENCE TO RELATED APPLICATION

This application is a continuation application of PCT/JP2017/008328 filed on Mar. 2, 2017 and claims benefit of Japanese Application No. 2016-170784 filed in Japan on Sep. 1, 2016, the entire contents of which are incorporated herein by this reference.

BACKGROUND OF THE INVENTION

Field of the Invention

Embodiments of the present invention relate to an electronic endoscope and an endoscope system, and in particular relate to an electronic endoscope and an endoscope system capable of automatically adjusting an amplification gain of an output video signal of an endoscope according to a level diagram of a processor.

Description of Related Art

In recent years, electronic endoscopes (hereinafter also referred to as scopes) have been widely used for diagnosis and treatment using treatment instruments in a medical field, and the like. An endoscope system is commonly used which is provided with an image pickup device such as a charge coupled device (CCD) at a distal end of an electronic endoscope, and displays an observed image picked up by using the CCD on a monitor with a video processor (hereinafter referred to as a processor).

The image pickup device outputs voltage proportional to an incident light amount until the incident light amount reaches a predetermined amount. Then, when the incident light amount has exceeded the predetermined amount, the output voltage loses linearity with respect to the incident light amount to be saturated at a predetermined level. In a conventional scope, a gain of a video signal has been adjusted so that a maximum output voltage at which linearity is held (hereinafter referred to as a linear saturation level) may become a maximum value of an output video signal from the scope. That is, an area which exceeds the linear saturation level and cannot maintain linearity has not been outputted from the scope to the processor. In addition, in a conventional processor, a gamma characteristic (hereinafter referred to as a gamma curve) has been set so that a maximum value of a video signal inputted from the scope may become a maximum value of an output video signal displayable on the monitor.

In addition, when a video signal is outputted from a next-generation scope to a next-generation processor, a gain of a video signal outputted from the scope is adjusted so that the linear saturation level of an output video signal from the scope may become a maximum value of an effective tone area of the monitor. That is, by outputting up to a voltage value at a level higher than the linear saturation level, a gain for a video signal outputted from the scope decreases, so that an S/N ratio can be improved.

In contrast, when a next-generation scope is connected to a conventional processor, since a gamma curve is set so that a maximum value of a video signal outputted from the scope may become a maximum value of a video signal to be outputted to the monitor, an area which cannot maintain linearity in excess of the linear saturation level is displayed in the effective tone area of the monitor, so that image quality may degrade. On the other hand, a scope has been proposed which is capable of switching a setting value related to processing of a video signal depending on a connected processor (see, for example, Japanese Patent Application Laid-Open Publication No. 2004-181231).

SUMMARY OF THE INVENTION

An electronic endoscope according to an aspect of the present invention is an electronic endoscope removably connected to a video processor in which a predetermined gamma characteristic is set, and includes: an image pickup device provided at a distal end of an insertion portion configured to be inserted into a subject, the image pickup device being configured to pick up an optical image of the subject to generate an image pickup signal; a gain circuit configured to amplify the image pickup signal using a predetermined gain parameter; a gamma characteristic recognition circuit configured to recognize the gamma characteristic of the video processor; and a gain adjustment circuit configured to set the gain parameter according to the gamma characteristic.

An endoscope system according to an aspect of the present invention includes: an electronic endoscope including an image pickup device provided at a distal end of an insertion portion configured to be inserted into a subject, the image pickup device being configured to pick up an optical image of the subject to generate an image pickup signal, and a gain circuit configured to amplify the image pickup signal using a predetermined gain parameter; and a processor in which a predetermined gamma characteristic is set and the processor is removably connected to the electronic endoscope. The processor acquires a linear saturation level of the image pickup signal in the electronic endoscope, calculates the gain parameter using the gamma characteristic, and amplifies the image pickup signal using the calculated gain parameter.

Furthermore, an electronic endoscope according to another aspect of the present invention is an electronic endoscope removably connected to a video processor in which a predetermined gamma characteristic is set, and the electronic endoscope includes: an image pickup device provided at a distal end of an insertion portion configured to be inserted into a subject, the image pickup device being configured to pick up an optical image of the subject to generate an image pickup signal; a gain circuit configured to amplify the image pickup signal using a predetermined gain parameter; and a processor including hardware. The processor recognizes the gamma characteristic of the video processor and sets the gain parameter according to the gamma characteristic.

DETAILED DESCRIPTION OF PREFERRED EMBODIMENTS

Embodiments of the present invention will be described below with reference to the attached drawings.

First Embodiment

Figure 1:
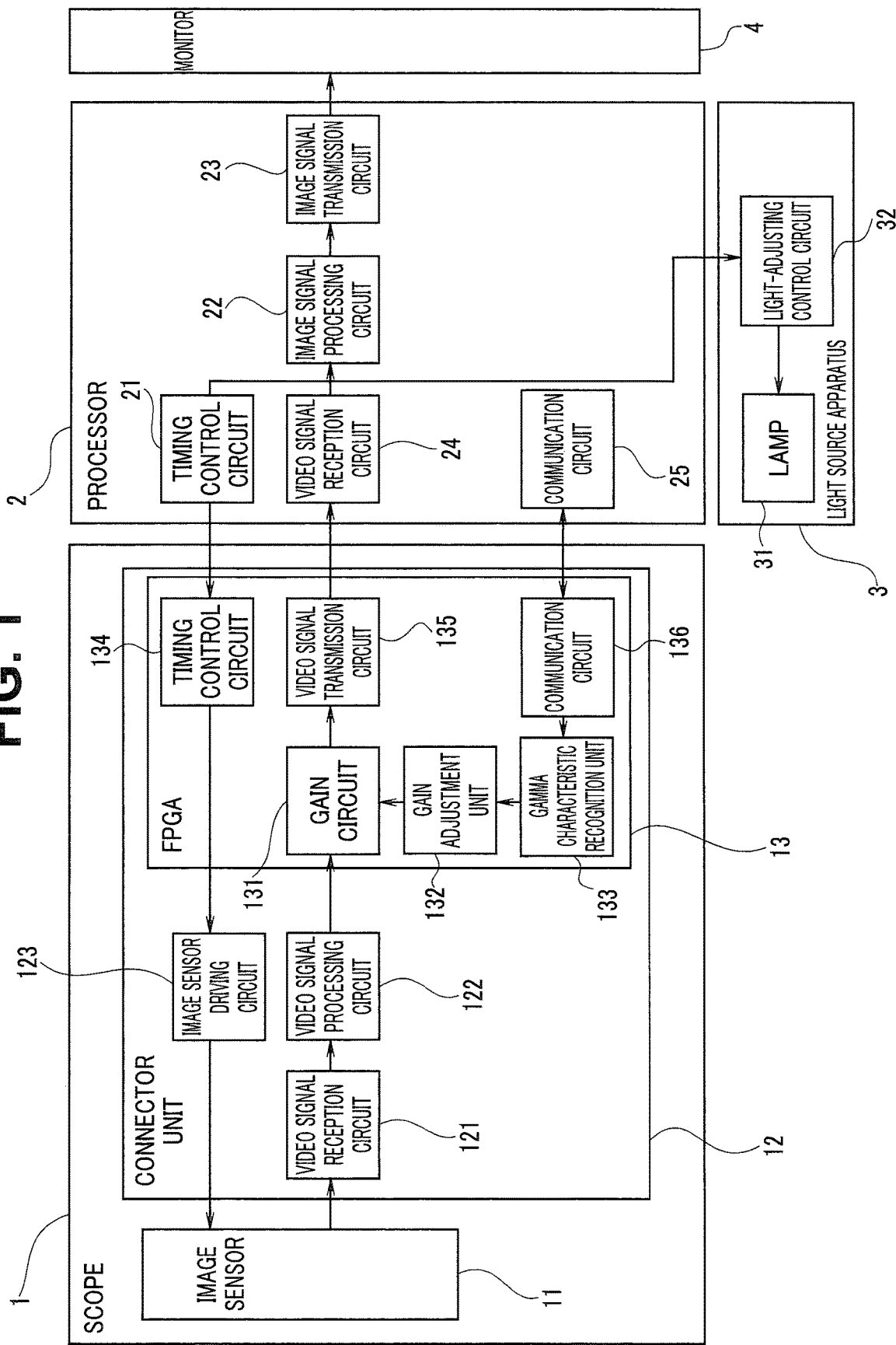
FIG. 1 is a block diagram for explaining an example of an overall configuration of an endoscope system according to a first embodiment of the present invention.

FIG. 1 is a block diagram for explaining an example of an overall configuration of an endoscope system according to a first embodiment of the present invention. For example, as shown in FIG. 1, the endoscope system of the first embodiment is configured to have a scope 1 to be inserted into a body cavity and observe or treat an affected part, and a video processor (hereinafter, referred to as a processor) 2 configured to perform predetermined signal processing on a video signal picked up by the scope 1. A monitor 4 configured to display video subjected to the signal processing, and a light source apparatus 3 configured to supply illumination light to the scope 1 are connected to the processor 2.

The scope 1 has an elongated insertion portion which can be inserted into a patient's body cavity or the like, and a distal end of the insertion portion is provided with an image sensor 11 such as a CCD as an image pickup device. The image sensor 11 picks up an optical image of a subject to output a predetermined video signal.

A proximal end side of the insertion portion is provided with a connector unit 12, and is configured to be removably connected to the processor 2. The connector unit 12 has an image sensor driving circuit 123, a video signal reception circuit 121, a video signal processing circuit 122, and an FPGA 13.

The image sensor driving circuit 123 receives a clock and a synchronization signal generated in a timing control circuit 21 of the processor 2 described later, generates a driving signal for driving the image sensor 11, and outputs the driving signal to the image sensor 11. The video signal reception circuit 121 receives a video signal outputted from the image sensor 11.

The video signal processing circuit 122 performs predetermined preprocessing on the video signal received in the video signal reception circuit 121. In the video signal reception circuit 121, processing such as pre-amplification processing, correlated double sampling processing, and A/D conversion processing is performed. Note that when the image sensor 11 is a CMOS image sensor, correlated double sampling processing and A/D conversion processing have already been performed in the image sensor 11. Accordingly, in the case, the processing is not performed in the video signal reception circuit 121.

A circuit for performing predetermined signal processing on a digital video signal and a circuit for transmitting/receiving a signal to/from the processor 2 are integrated into the FPGA 13. More specifically, respective elements of a timing control circuit 134, a communication circuit 136, a gamma characteristic recognition unit 133, a gain adjustment unit 132, a gain circuit 131, and a video signal transmission circuit 135 are integrated into the FPGA 13.

The timing control circuit 134 receives a clock and a synchronization signal generated in the timing control circuit 21 of the processor 2, and generates a predetermined processing pulse for each circuit in the FPGA 13. In addition, the timing control circuit 134 outputs the received clock and synchronization signal to the image sensor driving circuit 123.

The communication circuit 136 is a circuit for communicating various types of information with a communication circuit 25 of the processor 2. More specifically, when it is detected by electrical or mechanical determination means that the processor 2 has been connected to the scope 1, a gamma curve set in the processor 2 is transmitted from the communication circuit 25 to the communication circuit 136. Note that when a plurality of gamma curves are set in the processor 2, at least a gamma curve with a gentlest slope (a gamma curve with a lowest ratio of an output signal level to the monitor 4 with respect to an output signal level from the scope 1) is transmitted from the processor 2 to the communication circuit 136. For example, when a plurality of gamma curves are set in the processor 2 according to contrast settings for an image displayed on the monitor 4, at least a gamma curve used in a case of a setting of lowest contrast is transmitted.

The gamma characteristic recognition unit 133 extracts a gamma curve to be used for gain adjustment, when a plurality of gamma curves are received in the communication circuit 136. Note that a gamma curve with the gentlest slope of rising (a gamma curve with a lowest ratio of an output signal level to the monitor 4 with respect to an output signal level from the scope 1) is used for gain adjustment.

The gain adjustment unit 132 sets a gain parameter to be used in the gain circuit 131 based on the gamma curve extracted in the gamma characteristic recognition unit 133. More specifically, the gain parameter is set so that a linear saturation level in the video signal outputted from the scope 1 may become a maximum value of an effective tone area of the monitor 4 in the monitor output video signal level.

The gain circuit 131 uses the gain parameter set in the gain adjustment unit 132 to adjust an output level of the video signal received from the video signal processing circuit 122.

The video signal transmission circuit 135 transmits a video signal having a gain adjusted in the gain circuit 131 to the processor 2.

The processor 2 performs predetermined signal processing on the video signal inputted from the scope 1, and generates a video signal to be displayed on the monitor 4 for output to the monitor 4. The processor 2 has the timing control circuit 21, a video signal reception circuit 24, an image signal processing circuit 22, an image signal transmission circuit 23, and the communication circuit 25.

The timing control circuit 21 generates a clock signal at a predetermined frequency and a synchronization signal for output to the timing control circuit 134 of the scope 1. In addition, the clock signal and the synchronization signal generated in the timing control circuit 21 are outputted to the light source apparatus 3. The video signal reception circuit 24 receives a video signal having a gain adjusted in the FPGA 13 of the scope 1 for output to the image signal processing circuit 22.

The image signal processing circuit 22 performs various types of processing on the inputted video signal to generate a video signal to be displayed on the monitor 4. More specifically, the inputted video signal is subjected to white balance processing, color correction processing, distortion correction processing, and enhancement processing, or a selected gamma curve is used to convert a level of the video signal inputted from the scope 1 into a level of a video signal to be outputted to the monitor 4. The processed video signal is outputted to the monitor 4 via the image signal transmission circuit 23.

The communication circuit 25 is a circuit for communicating various types of information with the communication circuit 136 of the scope 1. More specifically, when the scope 1 and the processor 2 are connected to each other, a gamma curve set in the processor 2 is transmitted from the communication circuit 25 to the communication circuit 136.

The light source apparatus 3 has a light source such as a lamp 31 configured to generate illumination light, and a light-adjusting control circuit 32. Illumination light emitted from the lamp 31 is focused on an incident end face of a light guide of the scope 1. Note that, for example, an LED or a laser diode (semiconductor light source) may be used as the light source in addition to the lamp 31 shown in FIG. 1. In addition, when a semiconductor light source is used, a semiconductor light source which emits white light may be used, or it is possible to provide semiconductor light sources for respective color components of R (red), G (green) and B (blue), and combine light of the respective color components emitted from the semiconductor light sources to obtain white light. Or, images of R light, G light, and B light may be picked up in a time division manner to be combined through image processing (synchronization processing).

The light-adjusting control circuit 32 controls timing at which illumination light is emitted from the lamp 31 and a light amount.

Figure 2:
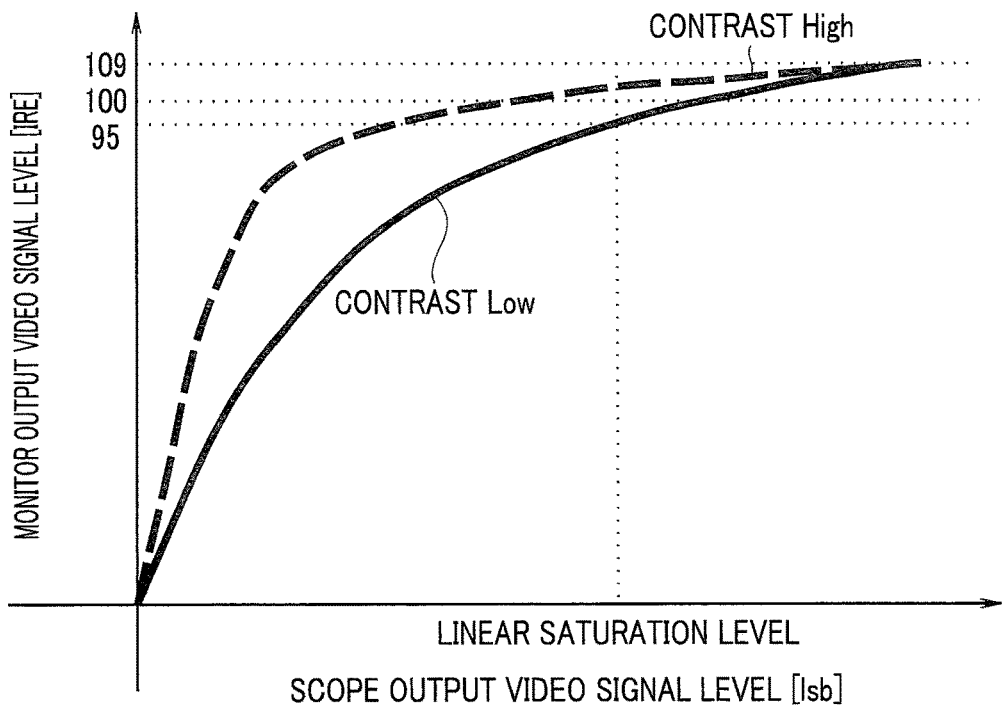
FIG. 2 is a diagram for explaining relationship between an output video signal level from a scope and an output video signal level to a monitor in a conventional endoscope system.
Figure 3:
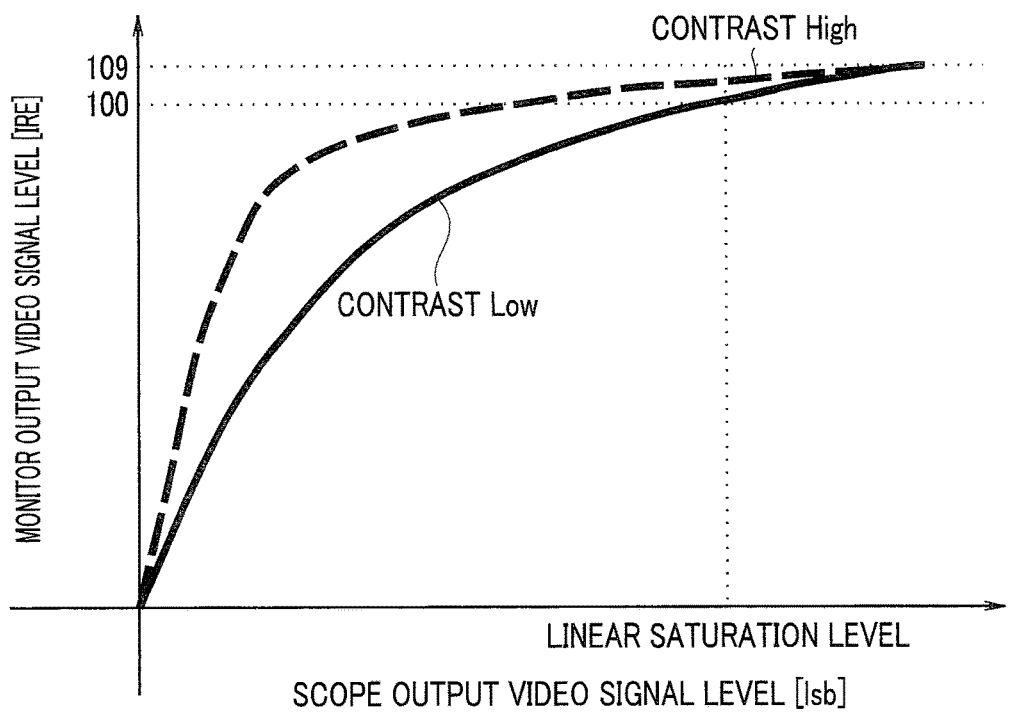
FIG. 3 is a diagram for explaining relationship between an output video signal level from a scope and an output video signal level to a monitor in the endoscope system of the present invention.

Next, a method of setting the gain parameter in the FPGA 13 of the scope 1 will be described using FIGS. 2 and 3. FIG. 2 is a diagram for explaining relationship between an output video signal level from a scope and an output video signal level to a monitor in a conventional endoscope system. FIG. 3 is a diagram for explaining relationship between an output video signal level from a scope and an output video signal level to a monitor in the endoscope system of the present invention.

Note that it is assumed that in both the endoscope systems in FIGS. 2 and 3, the effective tone area of a monitor is 0-100 IRE, and a maximum value of an output video signal displayable on the monitor is 109 IRE. In addition, it is assumed that both the endoscope systems in FIGS. 2 and 3 are configured by combining a next-generation scope (a scope of a type which outputs up to a signal at a high level exceeding the linear saturation level) and a conventional processor (a processor in which a gamma curve is set so that a maximum value of a video signal outputted from the scope may become a maximum value of a video signal to be outputted to the monitor).

In addition, it is assumed that in both the processors of the endoscope systems in FIGS. 2 and 3, two types of gamma curves are set which are a gamma curve used in displaying a low-contrast image on the monitor (a gamma curve of CONTRAST Low shown by a thick line in the figures) and a gamma curve used in displaying a high-contrast image on the monitor (a gamma curve of CONTRAST High shown by a thick dashed line in the figures).

As shown in FIG. 2, in the conventional endoscope system, a gamma curve is set so that a maximum value of a video signal outputted from the scope may become a maximum value of a video signal to be outputted to the monitor. That is, a gamma curve is set so that a maximum value of a video signal outputted from the scope may become 109 IRE. As shown in FIG. 2, in a gamma curve for high contrast with steep rising, a linear saturation level of a video signal outputted from the scope goes out of the effective tone area of the monitor (a value between 100 IRE and 109 IRE). Accordingly, only a video signal which is always equal to or lower than the linear saturation level and linearity of which is maintained is displayed in the effective tone area of the monitor.

However, in a gamma curve for low contrast with gentle rising, the linear saturation level of a video signal outputted from the scope falls within the effective tone area of the monitor (for example, 95 IRE). That is, an area which exceeds the linear saturation level and linearity of which cannot be maintained in a video signal outputted from the scope is also displayed in the effective tone area of the monitor.

So, as shown in FIG. 3, the endoscope system of the first embodiment increases the gain parameter by which a video signal is multiplied so that the linear saturation level of a scope output video signal in the gamma curve for low contrast may become equal to or greater than a maximum value of the effective tone area of the monitor (100 IRE) to set the gain parameter. By thus adjusting the gain parameter, only a video signal which is always equal to or lower than the linear saturation level and linearity of which is maintained is displayed in the effective tone area of the monitor. Accordingly, it is possible to prevent degradation of image quality of video displayed on the monitor 4.

Thus, according to the first embodiment, when the processor 2 is connected to the scope 1, the gamma curve set in the processor 2 is transmitted to the scope 1. The gain adjustment unit 132 of the scope 1 refers to the received gamma curve, and sets the gain parameter so that a value of the linear saturation level in a scope output video signal level may be converted into a value equal to or greater than the maximum value of the effective tone area in a monitor output video signal level. By using the gain parameter set in the gain adjustment unit 132 to adjust an output level of a video signal received from the video signal processing circuit 122, only a video signal which is always equal to or lower than the linear saturation level and linearity of which is maintained can be displayed in the effective tone area of the monitor, and therefore it is possible to prevent degradation of image quality of video displayed on the monitor 4.

Note that in the above description, regarding timing of transmitting the gamma curve, although the gamma curve is automatically transmitted when the scope 1 and the processor 2 are connected to each other, transmission may be performed at any timing such as when a user's instruction or a request from the scope 1 is received.

In addition, types of gamma curves set in the processor 2 are not limited to two types, and one type may be set, or three or more types may be set. Even when three or more types are set, gain adjustment is performed using a gamma curve with a smallest value of the monitor output video signal level corresponding to the linear saturation level in the scope output video signal level.

Second Embodiment

In the electronic endoscope of the first embodiment described above, the scope 1 receives a gamma curve from the processor 2 and adjusts the gain parameter. In contrast, the second embodiment is different in that the scope 1' receives information (e.g., ID) for identifying a connected processor 2, and sets a gain parameter based on the information.

Figure 4:
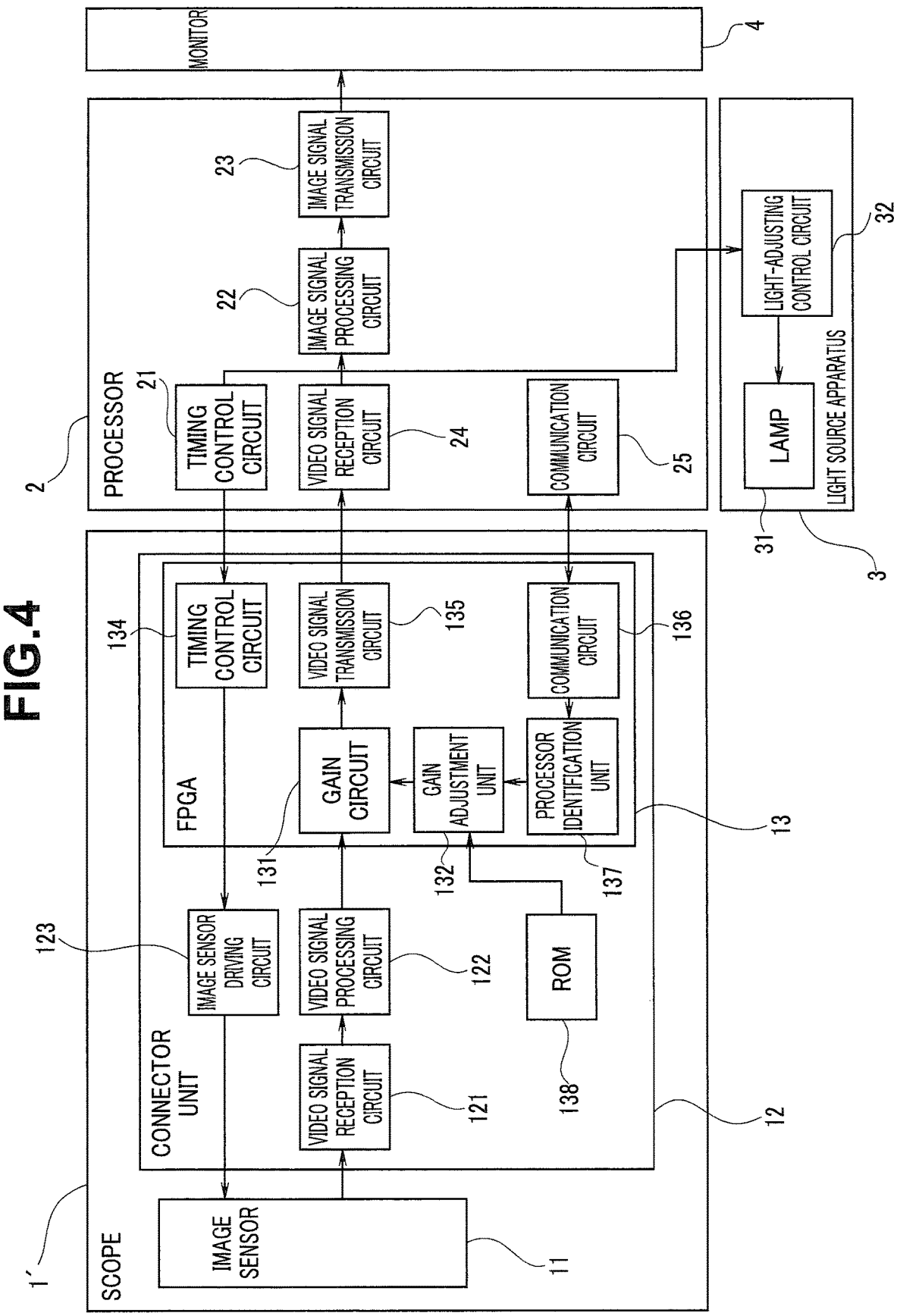
FIG. 4 is a block diagram for explaining an example of an overall configuration of an endoscope system according to a second embodiment.

FIG. 4 is a block diagram for explaining an example of an overall configuration of an endoscope system according to a second embodiment. The configuration of the endoscope system of the second embodiment is similar to the endoscope system according to the first embodiment described using FIG. 1 except that the scope 1' is provided with a ROM 138, and has a processor identification unit 137 instead of the gamma characteristic recognition unit 133. Hereinafter, a same component will be given a same sign, and description will be omitted.

The processor identification unit 137 identifies a type of the processor 2 connected to the scope 1'. For example, in a case where the processor 2 is given an ID and the type of the processor 2 can be identified by the ID information, when the processor 2 is connected to the scope 1', the processor identification unit 137 receives the ID information from the processor 2 through the communication circuits 25, 136. Note that the communication circuit 25 may be configured to transmit predetermined ID information to the communication circuit 136 under control of an unillustrated CPU of the processor 2. In addition, information other than an ID may be used to identify the type of the processor 2. The processor identification unit 137 outputs the identified type of the processor 2 to the gain adjustment unit 132.

The ROM 138 is a storage unit composed of a nonvolatile memory, and a gain parameter by which a video signal is multiplied is registered for each type of a processor 2 having a possibility of being connected to the scope 1'. A gain parameter registered in the ROM 138 is calculated in advance based on a gamma curve set for each type of a processor 2 so that a value of the linear saturation level in the scope output video signal level may be converted into a value equal to or greater than a maximum value of the effective tone area in the monitor output video signal level.

The gain adjustment unit 132 refers to the ROM 138 when information on the type of the processor 2 is inputted from the processor identification unit 137. Then, a gain parameter corresponding to the received type of the processor 2 is extracted from the ROM 138, and outputted to the gain circuit 131. The gain circuit 131 uses the gain parameter set in the gain adjustment unit 132 to adjust an output level of a video signal received from the video signal processing circuit 122.

Thus, according to the second embodiment, when the processor 2 is connected to the scope 1', information capable of identifying the type of the processor 2 such as a processor ID is transmitted to the scope 1. The gain adjustment unit 132 of the scope 1' refers to the ROM 138 to extract the gain parameter registered corresponding to the received information on the type of the processor 2. By using the gain parameter extracted in the gain adjustment unit 132 to adjust an output level of a video signal received from the video signal processing circuit 122, only a video signal which is always equal to or lower than the linear saturation level and linearity of which is maintained can be displayed in the effective tone area of the monitor, and therefore it is possible to prevent degradation of image quality of video displayed on the monitor 4.

According to the second embodiment, information from which the type of processor can be identified, such as a processor ID, should just be transmitted from the processor 2 to the scope 1', so that an amount of transmitted information can be reduced as compared to when transmitting a gamma curve itself. In addition, even when a plurality of gamma curves are set in the processor 2, it is not necessary to determine which gamma curve should be used to set the gain parameter, so that processing can be simplified. Furthermore, since a gain parameter is calculated in advance for each type of the processor 2 and registered in the ROM 138, it is not necessary for the gain adjustment unit 132 to calculate the gain parameter, and therefore processing can be simplified, so that processing efficiency improves.

Third Embodiment

In the endoscope system of the first embodiment described above, a gamma curve in the processor 2 is transmitted to the scope 1, and the gain parameter is calculated on the scope 1 side. In contrast, the third embodiment is different in that the linear saturation level in the scope output video signal level is transmitted from the scope 1" to the processor 2', and the gain parameter is calculated on the processor 2' side.

Figure 5:
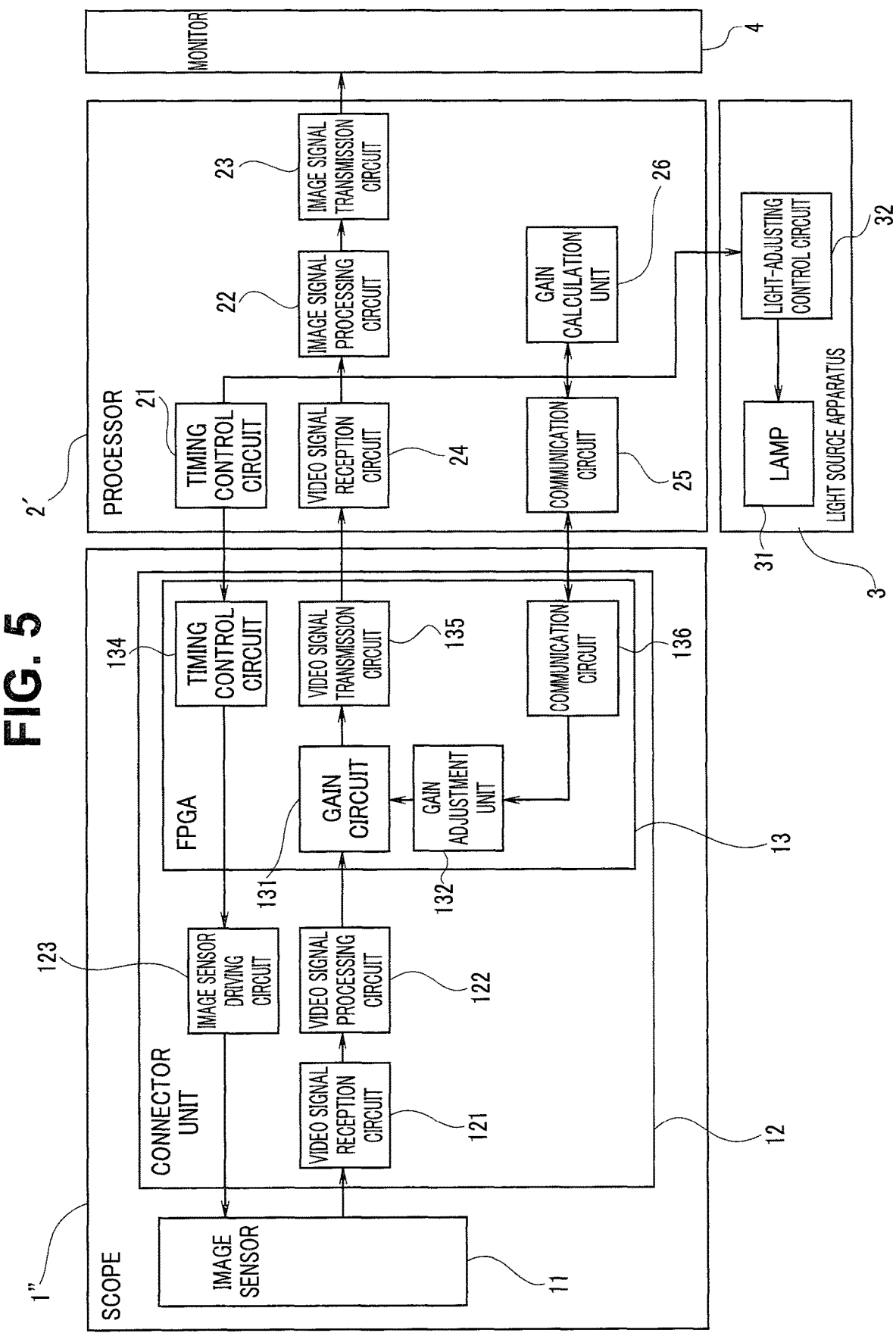
FIG. 5 is a block diagram for explaining an example of an overall configuration of an endoscope system according to a third embodiment.

FIG. 5 is a block diagram for explaining an example of an overall configuration of an endoscope system according to a third embodiment. The configuration of the endoscope system of the third embodiment is similar to the endoscope system according to the first embodiment described using FIG. 1 except that the gamma characteristic recognition unit 133 is deleted from the scope 1", and the processor 2' is provided with a gain calculation unit 26. Hereinafter, a same component is given a same sign, and description is omitted.

When the scope 1" is connected to the processor 2', the gain calculation unit 26 receives, from the scope 1" via the communication circuit 136 and the communication circuit 25, the linear saturation level of the video signal outputted from the scope 1". Then, a gamma curve set in the processor 2' is referred to, and a gain parameter is calculated which is required to convert the received linear saturation level into a value equal to or greater than a maximum value of the effective tone area in the monitor output video signal level. Note that when a plurality of gamma curves are set in the processor 2', a gamma curve with a gentlest slope of rising is used to calculate the gain parameter. The calculated gain parameter is outputted to the gain adjustment unit 132 of the scope 1" via the communication circuit 25 and the communication circuit 136.

The gain adjustment unit 132 outputs the gain parameter inputted from the processor 2' to the gain circuit 131. The gain circuit 131 uses the gain parameter inputted from the gain adjustment unit 132 to adjust an output level of a video signal received from the video signal processing circuit 122.

Thus, according to the third embodiment, it suffices that a gain parameter by which a video signal in the scope 1" is multiplied is calculated on the processor 2' side, and the scope 1" uses the gain parameter inputted from the processor 2' to adjust an output level of the video signal. Accordingly, since processing of calculating the gain parameter becomes unnecessary in the scope 1", circuit scale can be reduced.

Each "unit" in the present specification is a conceptual one corresponding to each function of the embodiments, and does not necessarily correspond to specific hardware or software routine on a one-to-one basis. Accordingly, in the present specification, the embodiments have been described assuming virtual circuit blocks (units) having respective functions of the embodiments. In addition, regarding each step in each procedure in the embodiments, the execution order may be changed, a plurality of steps may be simultaneously executed, or each step may be executed in a different order for each execution unless contrary to the nature. Furthermore, all or part of respective steps in respective procedures in the embodiments may be implemented by hardware.

Note that, in the above-described embodiments, description has been made on the examples in which recognition of the gamma characteristic and setting of the gain parameter are achieved by the circuits in the FPGA or the video processor. However, the above-described processing may be performed by a software in the FPGA or the video processor. For example, the video processor includes a processor for image processing, which includes hardware such as CPU, ROM, RAM, etc. A software program for the respective processing is stored in the ROM, and the respective image processing can be performed by reading out the software program by the CUP of the processor, developing the software program to the RAM, and executing the software program.

Although some embodiments of the present invention have been described, the embodiments are illustrated as examples, and are not intended to limit the scope of the invention. The novel embodiments can be implemented in various other forms, and various omissions, substitutions, or modifications are possible within a range not departing from the gist of the invention. The embodiments and variants are included in the scope and gist of the invention, and are included in the scope of the invention recited in the claims and equivalents.

What is claimed is:

1. An electronic endoscope removably connected to a video processor in which a predetermined gamma characteristic is set, the electronic endoscope comprising:
   an image pickup device provided at a distal end of an insertion portion configured to be inserted into a subject, the image pickup device being configured to pick up an optical image of the subject to generate an image pickup signal;
   a gain circuit configured to amplify the image pickup signal using a predetermined gain parameter;
   a gamma characteristic recognition circuit configured to recognize the gamma characteristic of the video processor; and
   a gain adjustment circuit configured to set the gain parameter according to the gamma characteristic.

2. The electronic endoscope according to claim 1, wherein the gamma characteristic recognition circuit acquires the gamma characteristic from the video processor.

3. The electronic endoscope according to claim 1, wherein the gamma characteristic recognition circuit acquires a type of the video processor from the video processor.

4. The electronic endoscope according to claim 3, further comprising
   a memory configured to record the gain parameter corresponding to the type of the video processor or the gamma characteristic, wherein the gain adjustment circuit extracts the gain parameter corresponding to a recognition result of the gamma characteristic recognition circuit.

5. The electronic endoscope according to claim 1, wherein the gain adjustment circuit sets the gain parameter so that in the gamma characteristic of the video processor, a linear saturation level of the image pickup signal is converted into an upper limit level of an effective tone area of a monitor to which a video signal is outputted from the video processor.

6. An endoscope system comprising:
   an electronic endoscope comprising an image pickup device provided at a distal end of an insertion portion configured to be inserted into a subject, the image pickup device being configured to pick up an optical image of the subject to generate an image pickup signal, and a gain circuit configured to amplify the image pickup signal using a predetermined gain parameter; and
   a processor in which a predetermined gamma characteristic is set, the processor being removably connected to the electronic endoscope,
   wherein the processor acquires a linear saturation level of the image pickup signal in the electronic endoscope, calculates the gain parameter using the gamma characteristic, and amplifies the image pickup signal using the calculated gain parameter.

7. The endoscope system according to claim 6, wherein the processor calculates the gain parameter so that in the gamma characteristic set in the processor, the linear saturation level of the image pickup signal is converted into an upper limit level of an effective tone area of a monitor to which a video signal is outputted from the processor.

8. An electronic endoscope removably connected to a video processor in which a predetermined gamma characteristic is set, the electronic endoscope comprising:
   an image pickup device provided at a distal end of an insertion portion configured to be inserted into a subject, the image pickup device being configured to pick up an optical image of the subject to generate an image pickup signal;
   a gain circuit configured to amplify the image pickup signal using a predetermined gain parameter; and
   a processor including hardware,
   wherein the processor recognizes the gamma characteristic of the video processor and sets the gain parameter according to the gamma characteristic.

* * * * *